United States Patent [19]

Angulo

[11] Patent Number: 4,474,180

[45] Date of Patent: Oct. 2, 1984

[54] APPARATUS FOR DISINTEGRATING KIDNEY STONES

[75] Inventor: Earl D. Angulo, Silver Spring, Md.

[73] Assignee: The United States of America as represented by the Administrator of the National Aeronautics and Space Administration, Washington, D.C.

[21] Appl. No.: 377,891

[22] Filed: May 13, 1982

[51] Int. Cl.³ .............................................. A61B 17/00
[52] U.S. Cl. .................................... 128/328; 128/24 A
[58] Field of Search ............. 128/24 A, 328; 269/246, 269/249, 270; 248/49, 632, 634, 559; 403/391, 362; 339/272 R, 272 A, 272 UC, 242, 276 T

[56] References Cited

U.S. PATENT DOCUMENTS

| 297,884 | 4/1884 | Warfield | 269/246 X |
|---|---|---|---|
| 836,376 | 11/1906 | Fancher | 279/83 |
| 1,867,359 | 7/1932 | Higby | 279/9 |
| 2,127,050 | 8/1938 | Smith | 339/276 |
| 3,565,062 | 2/1971 | Kuris | 128/24 A |
| 3,618,594 | 11/1971 | Banko | 128/24 A |
| 3,830,240 | 8/1974 | Antonevich et al. | 128/328 |
| 3,861,391 | 1/1975 | Antonevich et al. | 128/328 |
| 3,934,316 | 1/1976 | Driscoll | 269/249 X |

FOREIGN PATENT DOCUMENTS 24505 of 1908 United Kingdom ......... 339/272 UC

Primary Examiner—Kyle L. Howell
Assistant Examiner—Christine A. Fukushima
Attorney, Agent, or Firm—John O. Tresansky; Sol Sheinbein

[57] ABSTRACT

The useful life of the wire probe in an ultrasonic kidney stone disintegration instrument is enhanced and prolonged by attaching the wire (24) of the wire probe to the tip (26) of an ultrasonic transducer (28) by means of a clamping arrangement comprising opposing set screws (60, 65), one (60) of which is adapted to accept the clamping load from the other set screw (65) without deforming the wire by machining a pair of mutually transverse grooves (64) in the inner end face (62) of the screw (60) which is adapted to accept and hold the wire probe along the central longitudinal axis (52) of the transducer tip which is adapted to impart ultrasonic energy to the wire. Additionally, damping material is applied to the wire probe (24) in the form of a damper tube (70) through which the wire probe passes in the region adjacent the transducer tip. The damper tube extends outwardly from the transducer tip (26) a predetermined distance, terminating in a resilient soft rubber joint (72). Also, the damper tube is supported intermediate its length by a support member (82). The damper system thus provided acts to inhibit lateral vibrations of the wire in the region of the transducer tip (26) while providing little or no damping to the linear vibrations imparted to the wire (24) by the transducer (28).

18 Claims, 7 Drawing Figures

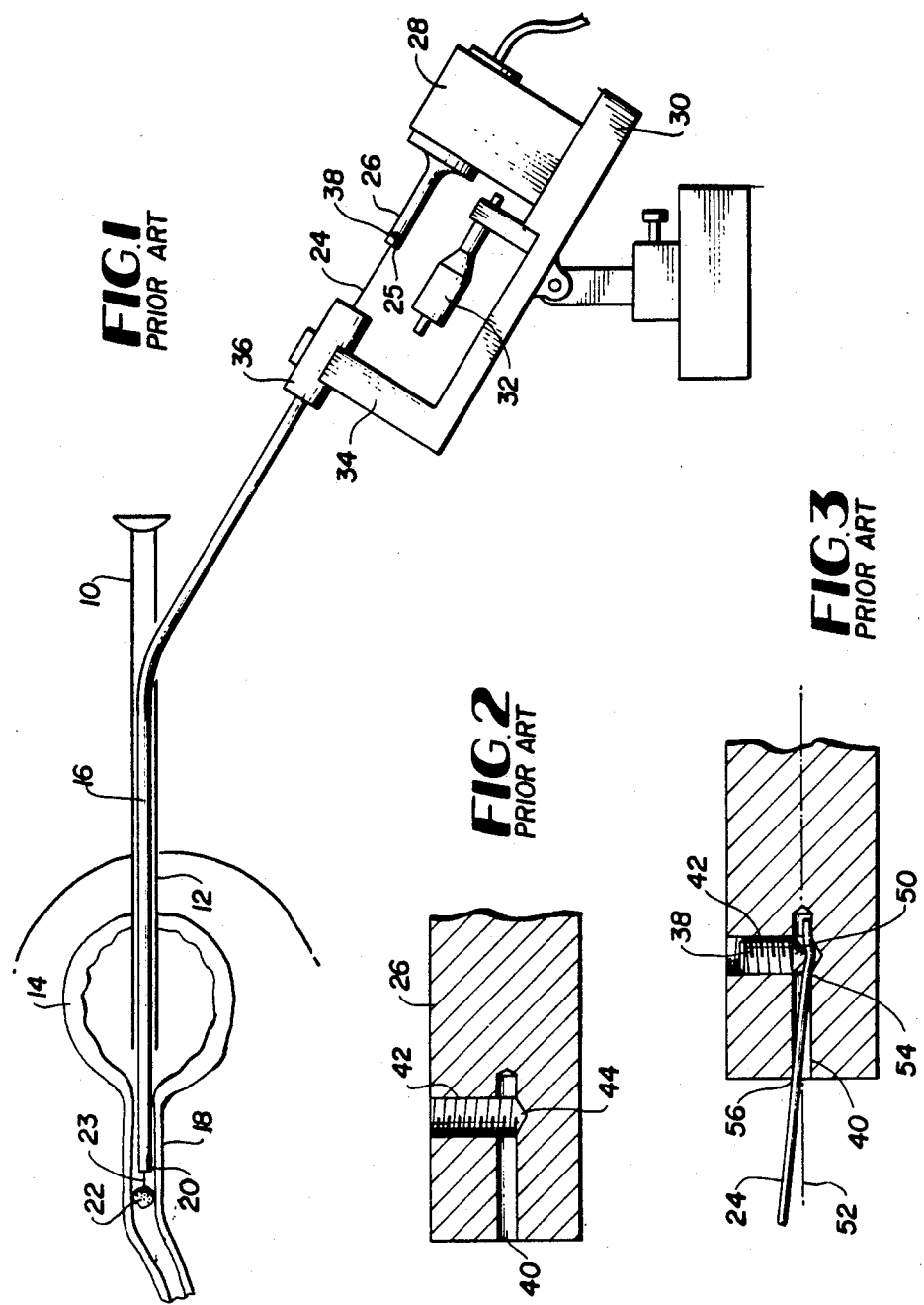

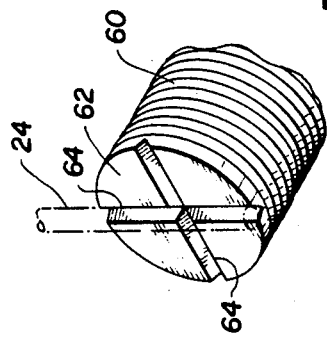
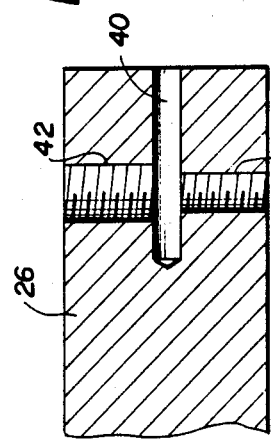
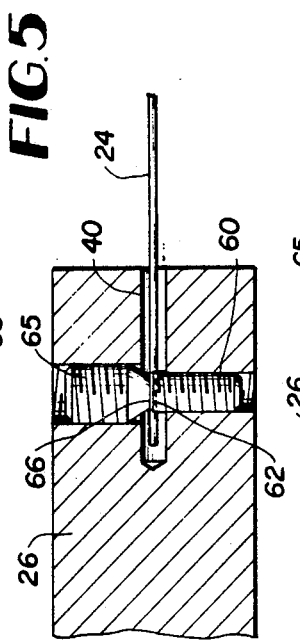
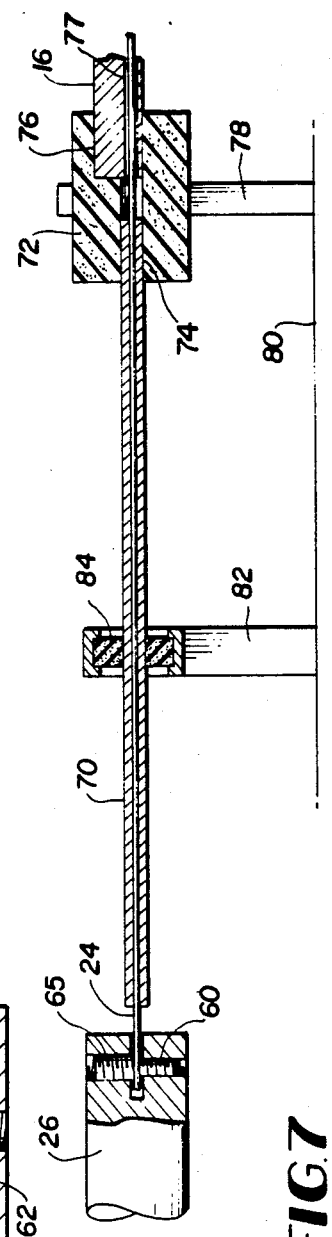

APPARATUS FOR DISINTEGRATING KIDNEY STONES

ORIGIN OF THE INVENTION

The invention described herein was made by an employee of the U.S. Government and may be manufactured and used by or for the Government for governmental purposes without the payment of any royalties thereon or therefor.

TECHNICAL FIELD

The invention relates generally to a mechanical system for disintegrating urinary calculi and more particularly to ultrasonic apparatus for fragmenting urinary calculi in situ.

BACKGROUND ART

The incidence of hospitalization for the removal of urinary calculi, commonly referred to as kidney stones, has been estimated to be as high as 200,000 cases per year. A vast majority of these patients pass their stones spontaneously; however, in the remainder, the kidney stone(s) become impacted in the ureter, a muscle tube joining the kidney to the bladder. An impacted kidney stone is a source of intense pain and bleeding, a source of infection and, if a stone completely blocks the flow of urine for any extended length of time, can cause a loss of a kidney. Small stones which are lodged in the lower one third of the ureter can frequently be removed non-surgically using a technique employing a well known Dormia stone basket. This procedure is successful in approximately 50% of the cases. However, basket removal of a kidney stone usually fails if the stone is lodged in the upper ureter, is impacted, or is in the order of 1.0 cm in size. In these cases the only procedure by which the stone could heretofore be removed was through a major operation called a ureterolithotomy.

More recently, however, a non-surgical method for removing kidney stones has been developed wherein a catheter is placed cystoscopically at the site of the stone in the urinary tract, after which a long wire probe, acting as an ultrasonic waveguide, is passed through a lumen of the catheter and is brought into contact with the stone. The wire probe is attached to an ultrasonic transducer which, when energized, sets the wire probe into longitudinal and transverse vibrations. The vibrational energy is transmitted to the stone, causing it to fracture into small fragments which the patient can then pass spontaneously after withdrawal of the catheter.

While such apparatus is adapted to operate as intended, a severe limitation has been found to exist due to premature breakage of the wire probe at the point of connection to the tip of the ultrasonic transducer. The vibrational energy, typically 20KHz in frequency, causes the wire probe to snap off after 15 or 20 seconds of operation. This has been found to be insufficient time to complete a kidney stone disintegration procedure, even though the stone will fracture after as little as about 10 seconds of contact with the wire probe. What is required is a means to prolong the operational life of the wire probe for a length of time adequate for completion of the procedure. A desirable time frame is typically 1 minute, which is an order of magnitude greater than that currently provided by known prior art apparatus.

STATEMENT OF INVENTION

Accordingly, it is an object of the present invention to provide an improvement in ultrasonic instrumentation for disintegrating urinary calculi or kidney stones.

Another object is to provide an improved mechanical system for prolonging the operational life of an instrument for disintegrating kidney stones.

Still another object is to provide a means for reducing the relatively high mechanical stresses encountered in an ultrasonic kidney stone disintegration instrument.

And yet another object is to provide an improved ultrasonic instrument for disintegrating kidney stones which obviates the problem of metal fatigue which would otherwise cause premature termination of a medical procedure utilized for the removal of kidney stones.

These and other objects are provided by a mechanical system for prolonging the life of an instrument for disintegrating urinary calculi or kidney stones wherein the instrument includes a wire probe connected to an ultrasonic transducer and which is fed through a catheter to the site of the kidney stone. The coupling between the transducer and the wire probe comprises clamping means at the tip of the transducer including a pair of opposing screw type members, one of which acts as an anvil for accepting the clamping load from the other member while preventing deformation of the wire probe at the point of clamping. Also included is damping means located along a predetermined length of the wire adjacent the transducer tip for inhibiting lateral vibration of the wire when driven by the transducer.

The foregoing as well as other objects, features and advantages of the invention will become apparent from the following detailed description when taken in conjunction with the appended drawings.

BRIEF DESCRIPTION OF DRAWINGS

FIG. 1 is a side elevational view of apparatus in accordance with the prior art for fragmenting kidney stones.

FIG. 2 is a partial longitudinal sectional view of an ultrasonic transducer tip in accordance with the prior art.

FIG. 3 is a partial longitudinal sectional view of a prior art transducer tip illustrating the manner in which a wire probe is clamped therein.

FIG. 4 is a partial longitudinal sectional view of a transducer tip in accordance with the subject invention.

FIG. 5 is a partial longitudinal sectional view of the transducer tip as shown in FIG. 4 and being illustrative of the manner in which a wire probe is clamped in accordance with the subject invention.

FIG. 6 is a partial perspective view of the anvil portion of the clamping means shown in FIG. 5.

FIG. 7 is a partial side elevational view of vibrational damping means forming a part of the subject invention.

DETAILED DESCRIPTION OF THE INVENTION

Refer now to the drawings and, more particularly, to FIG. 1, where there is illustrated an ultrasonic kidney stone disintegration instrument in accordance with the prior art. The purpose of this Figure is to provide a better understanding of the invention to be described in detail when FIGS. 4 through 7 are considered. As illustrated in FIG. 1, a cystoscope 10 is shown inserted through a urethra 12 and into a bladder 14. A catheter 16 is inserted through the cystoscope 10, the bladder 14 and into a ureter 18 until its far end 20 comes into proximity to a piece of urinary calculi, hereinafter referred to as a kidney stone 22. An ultrasonic waveguide in the form of a wire probe 24 is inserted through one of eight lumens in the catheter 16 until its far end 23 contacts the stone 22. The diameter of the wire probe 24 is of a substantially smaller diameter than the lumen diameter of the catheter 16 so that any movement of the wire probe is not restricted by the catheter material. The opposite or near end 25 of the wire probe 24 is connected to the tip 26 of an ultrasonic transducer assembly 28 which is mounted on a base 30. The base 30 includes a micrometer 32 which is connected to the transducer 28 for adjusting the position of the wire probe 24 against the stone 22 by a linear translation of the transducer assembly 28 on the base 30. The base 30 additionally includes an outward angular support member 34 which includes a connector element in the form of a catheter joint 36 for engaging and holding the near end of the catheter 16. As shown in FIG. 1, the wire probe 24 is clamped to the end of the transducer 26 by means of a set screw 38 which leads now to consideration of FIGS. 2 and 3.

Referring now to FIG. 2, the transducer tip 26 which is partially shown in section includes a central longitudinal axial bore 40 which is adapted to receive the probe wire 24 (FIG. 1), not shown. The tip 26 additionally includes a threaded screw hole 42 which runs mutually transverse to and through the axial bore 40, terminating in a cone point 44 which results from the drill and/or tap used for making the screw hole.

Referring now to FIG. 3, it can be seen that when the wire probe 24 is inserted into the bore 40 and then clamped by means of the set screw 38 inserted into the threaded screw hole 42, the tip 50 of the set screw 38 causes a crimping of the end of the wire probe 24 into the cone point 44, which causes the probe wire 24 to become offset relative to the central longitudinal axis 52 of the transducer tip 26. As a consequence, a relatively high mechanical stress is induced into the wire probe at point 54. This condition has been found to be the primary source of premature breakage when subjected to lateral vibration from the transducer 28 (FIG. 1). Additionally, the undamped motion of the vibrating wire at the point 56 where it emerges from the transducer tip 26 also contributes to the metal fatigue problem causing the wire probe to break.

With the foregoing in mind, the invention is directed to overcoming the problem of premature breakage of the wire probe 24 through the addition of two structural components, one of which prevents deformation of the wire probe at the point of clamping, while the other inhibits lateral vibration of the wire probe in the area where it is being driven by the ultrasonic transducer.

With respect to the first feature, as illustrated in FIGS. 4 and 5, the transducer tip 26 is modified to include a second threaded screw hole 58 diametrically opposed to the threaded screw hole 42 and which extends into the longitudinal bore 40. The threaded screw hole 58 is adapted to accept a second set screw, one with fine threads, which is shown by reference numeral 60 in FIG. 5. Further, the set screw 60, as shown in FIG. 6, includes a flattened end portion 62 having a surface which includes at least one, but preferably a pair of mutually transverse shallow grooves 64 forming a + which are adapted to accommodate and thus act as an anvil for the end portion of the wire probe 24 when inserted in the bore 40. The axis of the wire probe 24 can be controlled and easily centered since the anvil face 62 is adjustable by the turning of the set screw 60 and thus the axis of the wire can be moved up or down to coincide with the central longitudinal axis 52 (FIG. 3) of the axial bore 40. Whereas in the prior art apparatus the set screw 38, as shown in FIG. 3, typically includes a spherical tip, the type of set screw employed by the subject invention is a set screw 65 with a flat tip 66, thus removing the tendency for crimping the wire probe 24 at the point of contact with the wire and/or anvil face portion of the opposing set screw 60. It should be noted that the addition of the second set screw 60 does not unbalance the tuned mass of the transducer assembly which includes the tip portion 26. This is in contrast to earlier attempts which added a wire clamping fixture to the external tip 26 of the transducer. Such an arrangement caused an unbalance in the system, resulting in the loss of energy in the wire probe.

Referring now to FIG. 7, the second feature of the invention is directed to the utilization of a damper tube member 70, typically 3" to 4" in length, which is placed over the external portion of the wire probe 24 in the region where the wire probe emerges from the transducer tip 26, and extends outwardly therefrom terminating in a block of relatively thick, soft rubber 72 which has two offset bores 74 and 76 formed therein with the latter adapted to accommodate a catheter 16 with an off axis wire lumen 77 shown in FIG. 7. The soft rubber block 72 is adapted to act as a damper and catheter joint, and is held in position by a support member 78 which is secured to a base member 80. Base member 80 corresponds, for example, to the base member 30 shown in FIG. 1. In order to provide additional support for the damper tube 70 an intermediate damper tube support member 82 including a rubber bushing 84 is placed approximately midway between the transducer tip 26 and the member 72.

In such a configuration, the linear vibrations imparted by the transducer assembly 28, including the transducer tip 26, are not significantly damped but are transmitted along the wire probe 24 and out of the damper tube 70. At that point, i.e. in the region of the damper and catheter joint 72, the vibrational energy is free to induce the desired random lateral motion in the wire probe 24 necessary to shatter kidney stones. Additionally, the high mechanical stress caused at the point of clamping the wire 24 to the transducer tip 26 as well as the undamped motion of the vibrating wire where it exits from the transducer contributing to the metal fatigue problem have been alleviated.

The advantage of the ultrasonic kidney stone disintegration instrument modified in accordance with the teachings of this invention is a sizable increase in instrument lifetime, typically by a factor of fifteen or more.

In summation, what has been shown and described is an improvement in an instrument for disintegrating kidney stones by the introduction of a grooved adjustable anvil in the transducer tip at the clamping point of the wire probe to lessen concentrated stresses in the wire as well as the introduction of a vibrational damper system which minimizes lateral wire motion at the transducer tip while nevertheless transmitting linear motion thereto which acts to prolong the useful life of the wire probe.

Having thus shown and described the invention in its specific detail, the same has been provided by way of explanation and not limitation and accordingly all modifications, alterations and changes coming within the spirit and scope of the invention are herein meant to be included.

I claim:

1. An apparatus for disintegrating urinary calculi such as kidney stones or the like lodged in the urinary tract, comprising:
   catheter means;
   waveguide means (24) fed through said catheter and brought into contact with the calculi (22) to be removed;
   ultrasonic transducer means (28) coupled to said waveguide means (24) for imparting vibrations thereto;
   vibrational output means (26) forming a portion of said ultrasonic transducer means (28);
   clamping means coupling said waveguide means (24) to said output means (26) comprising a pair of movable oppositng members (60, 65) at said output means which are adapted to be brought together such that one of said members (60) acts as an anvil for accepting the clamping load applied by the other (65) of said members on said waveguide means thereby preventing any substantial deformation of said waveguide means at the point of clamping (54); and
   vibrational damping means (70, 72, 84) located adjacent said output means (26) and contacting said waveguide means for inhibiting lateral vibration of said waveguide means (24) in the region where said waveguide means leaves said output means while allowing substantially unimpaired longitudinal vibration thereof.

2. The apparatus as defined by claim 1 wherein said waveguide means (24) comprises a wire probe which is clamped to said output means (26) and fed through said catheter (16).

3. The apparatus as defined by claim 2 wherein said output means (26) includes a central longitudinal bore (40) formed in the end portion thereof for receiving said wire probe (24) and wherein said clamping means comprises a pair of members (60, 65) which are located in said end portion transverse to said longitudinal bore.

4. The apparatus as defined by claim 3 wherein said pair of members comprises a pair of screw type members fitted into respective threaded holes (42, 58) formed in the end portion of the output means (26) transverse to said longitudinal bore (40).

5. The apparatus as defined by claim 4 wherein said pair of screw type members comprise a first screw (60) having an inner end face (62) which includes at least one groove (64) formed therein for receiving and positioning said wire probe (24) in said longitudinal bore (40), and a second screw (65) having a flat inner end face (66) which is adapted to abut the grooved end face (62) of said first screw and said wire probe.

6. The apparatus as defined by claim 5 wherein said end face (62) of said first screw (60) includes a second groove (64) substantially transverse to said one groove.

7. The apparatus as defined by claim 4 wherein said screw type members comprise a first screw (60) having an end surface (62) including a linear groove (64) for accepting said wire probe (24) and acting as said anvil therefor and a second screw (65) having a flat end surface (66) opposing the end surface (62) of said first screw.

8. The apparatus as defined by claim 1 wherein said vibrational damping means comprises a predetermined length of vibrational damping material (70) located around said waveguide means (24).

9. The apparatus as defined by claim 8 wherein said waveguide means comprises a wire (24) and wherein said damping means comprises a sleeve (70) of damping material of a predetermined length fitted around said wire (24) in the region where said wire leaves said output means (26).

10. The apparatus as defined by claim 9 wherein said sleeve (70) comprises a tube of soft resilient material.

11. The apparatus as defined by claim 10 wherein said sleeve (70) comprises a tube of relatively tight fitting rubber.

12. The apparatus as defined by claim 11 wherein said sleeve (70) is comprised of relatively soft rubber, being 3 to 4 inches in length and terminating in a coupling member (72), said coupling member additionally including means (76) for accepting and holding the near end of the catheter.

13. The apparatus as defined by claim 12 wherein said coupling member (72) is comprised of resilient damping material.

14. The apparatus as defined by claim 12 wherein said coupling member (72) comprises a block of relatively soft rubber having a pair of offset bores (74, 76) formed therein, one (74) for receiving said damper tube (70) and said wire (24) and the other (70) for receiving said catheter (16) and said wire (24).

15. The apparatus as defined by claim 12 and additionally including a damper tube support member (82) located between the end of said output means (26) and said coupling member (72).

16. The apparatus as defined by claim 15 wherein said damper tube support member (82) additionally includes a resilient bushing member (84) which is adapted to encircle and hold said damper tube (70).

17. The apparatus as defined by claim 16 wherein said damper tube support member (82) is located substantially midway between said output means (26) and said coupling member (72).

18. Apparatus for dislodging calculi lodged in the urinary tract, comprising:
   a catheter adapted to be inserted into a ureter to abut the calculi to be dislodged;
   waveguide means comprising a wire probe fed through said catheter and brought into contact with the calculi to be dislodged;
   ultrasonic transducer means coupled to said waveguide means for imparting vibrations thereto; and
   clamping means coupling said waveguide means to said transducer means and comprising first and second movable opposing members adapted to be brought together whereby said first member acts as a support for accepting a clamping action applied by said second member on said waveguide means, said clamping means comprising a pair of screw members located in said transducer means, said first member including one groove formed in the end thereof and a second groove substantially transverse to said one groove for receiving said wire probe, said second member having a flat inner end face adapted to abut said grooved end face and said wire probe.

* * * * *